United States Patent [19]

Pelosi, Jr.

[11] 4,066,671

[45] Jan. 3, 1978

[54] (2,2-DIETHOXYETHYL)DIMETHYL[5-(4-NITROPHENYL)-2-FUROYLMETHYL]AMMONIUM CHLORIDE HEMIHYDRATE

[75] Inventor: Stanford S. Pelosi, Jr., Norwich, N.Y.

[73] Assignee: Morton-Norwich Products, Inc., Norwich, N.Y.

[21] Appl. No.: 766,123

[22] Filed: Feb. 7, 1977

[51] Int. Cl.² .......................................... C07D 307/52
[52] U.S. Cl. ................................. 260/347.7; 424/285
[58] Field of Search ...................................... 260/347.7

[56] References Cited

U.S. PATENT DOCUMENTS 3,096,348   7/1963   Denss et al. .................. 260/347.7

OTHER PUBLICATIONS

Dunlop, *The Furans*, ACS Monogram Series (1953), p. 431.

*Primary Examiner*—Richard L. Raymond
*Attorney, Agent, or Firm*—Anthony J. Franze

[57] ABSTRACT

(2,2-Diethoxyethyl)dimethyl[5-(4-nitrophenyl)-2-furoylmethyl]ammonium chloride hemihydrate is an effective antispasmodic agent.

1 Claim, No Drawings

(2,2-DIETHOXYETHYL)DIMETHYL[5-(4-NITROPHENYL)-2-FUROYLMETHYL]AMMONIUM CHLORIDE HEMIHYDRATE

This invention relates to the compound (2,2-diethoxyethyl)dimethyl[5-(4-nitrophenyl)-2-furoylmethyl]ammonium chloride hemihydrate, and a method for its preparation.

The compound of this invention possesses valuable pharmacologic properties. It is capable in a dose of 3 mcg/ml of inhibiting by 58% contractile responses of the isolated rabbit ileum to transmural electrical stimulation thus displaying antispasmodic properties.

The compound of this invention is readily prepared. Currently, it is preferred to react chloromethyl 5-(4-nitrophenyl)-2-furyl ketone with dimethylaminoacetaldehyde diethyl acetal in the presence of a solvent such as ethanol.

In order that this invention may be fully available to and understood by those skilled in the art, the method now preferred for making it is described:

Dimethylaminoacetaldehyde diethyl acetal (29 g, 0.18 mole) was added dropwise to a stirred mixture of 40 g (0.15 mole) of chloromethyl 5-(4-nitrophenyl)-2-furyl ketone in 750 ml of absolute ethanol at 30° over 15 minutes. The mixture was heated under reflux for 22 hrs and was filtered hot to remove a black insoluble material. The filtrate was cooled in ice, and the brown solid was filtered and discarded. The filtrate was diluted with 1.5 liters of anhydrous ether, and the solid which was deposited was collected by filtration to give 45 g (69%) of (2,2-diethoxyethyl)dimethyl[5-(4-nitrophenyl)-2-furoylmethyl] ammonium chloride hemihydrate. Two recrystallizations from $CH_3CN$ gave an analytical sample, m.p. 113°–118°.

Anal. Calcd. for $C_{20}H_{27}ClN_2O_6 \cdot \frac{1}{2} H_2O$: C, 55.11; H, 6.47; N, 6.43. Found: C, 55.19; H, 6.54; N, 6.45.

What is claimed is:

1. The compound (2,2-diethoxyethyl)dimethyl[5-(4-nitrophenyl)-2-furoylmethyl]ammonium chloride hemihydrate.

* * * * *